United States Patent [19]
Tokitoh et al.

[11] Patent Number: 4,808,756
[45] Date of Patent: Feb. 28, 1989

[54] METHOD FOR PRODUCTION OF α,ω-DIALDEHYDES

[75] Inventors: Yasuo Tokitoh; Noriaki Yoshimura, both of Kurashiki, Japan

[73] Assignee: Kuraray Co., Ltd., Kurashiki, Japan

[21] Appl. No.: 104,988

[22] Filed: Oct. 6, 1987

[30] Foreign Application Priority Data

Apr. 7, 1986 [JP] Japan .................................. 61-80347

[51] Int. Cl.$^4$ ............................................. C07C 45/50
[52] U.S. Cl. .................................... 568/454; 568/451; 568/494
[58] Field of Search ............... 568/454, 492, 494, 458, 568/462, 451, 454, 462, 458, 494

[56] References Cited

U.S. PATENT DOCUMENTS 4,248,802  2/1981  Kuntz ................................. 568/454
4,507,508  3/1985  Hayden et al. ..................... 568/494
4,742,178  5/1988  Nelson et al. ...................... 568/454

FOREIGN PATENT DOCUMENTS 0088955  9/1983  European Pat. Off. ............ 568/454

Primary Examiner—Werren B. Lone
Attorney, Agent, or Firm—Oblon, Fisher, Spivak, McClelland & Maier

[57] ABSTRACT

The method for producing α,ω-dialdehydes from α,ω-diolefins or α,ω-alkenals in good yield and with high efficiency. The expensive rhodium catalyst for hydroformylation can be reused without any substantial attrition of activity. Moreover, since the loses of the catalyst, monodentate phosphine and sulfolane used in the hydroformylation reaction are minimal, the method is commercially advantageous.

15 Claims, No Drawings

METHOD FOR PRODUCTION OF α,ω-DIALDEHYDES

BACKGROUND OF THE INVENTION

1. Field of the Invention

This invention relates to a method of producing α,ω-dialdehydes containing 8 to 12 carbon atoms and more particularly to a method of producing an α,ω-dialdehyde of 8 to 12 carbon atoms which comprises hydroformylating an α,ω-diolefin of 6 to 10 carbon atoms or an α,ω-alkenal of 7 to 11 carbon atoms and extracting the resulting reaction mixture.

The α,ω-dialdehyde of 8 to 12 carbon atoms, which is obtainable in accordance with this invention, is a compound of great use as an immobilizing agent for proteins and enzymes, a germicide, a high polymer crosslinking agent, or a strting material for the synthesis of the corresponding dicarboxylic acid, diol or diamine.

2. Description of the Prior Art

It is known that an α,ω-dialdehyde can be produced by hydroformylating an α,ω-diolefin or α,ω-alkenal of 6 to 10 carbon atoms with a mixture of hydrogen and carbon monoxide in the presence of a tertiary phosphine-modified rhodium compound as a catalyst. Because the rhodium catalyst used for this hydroformylation reaction is expensive, the commercial working of this known method calls for the separation of the rhodium catalyst from the product α,ω-dialdehyde for re-use, without entailing its loss and inactivation, in the subsequent hydroformylation reaction. In order to separate the rhodium catalyst from the product α,ω-dialdehyde by distillation, the reaction mixture must be heated to a high temperature, as high as to distill the highboiling α,ω-dialdehyde. Therefore, the rhodium catalyst undergoes pyrolysis in the course of distillation to cause precipitation of rhodium metal or degradation of the catalyst by byproduct high-boiling compounds so that the distillation residue containing the catalyst cannot be reused by recycling for a sufficiently long time. Therefore, as a method for avoiding the inactivation of the rhodium catalyst in separating it from the α,ω-dialdehyde following the hydroformylation reaction, it has been proposed to extract the hydroformylation reaction mixture (for example, U.S. Pat. No. 4,248,802, Japanese Patent Application Laid-Open No. 21638/1983, No. 157739/1983, No. 216138/1983) Japanese Patent Application Laid-Open No. 167937/1982 (corresponding to U.S. Pat. No. 4,248,802) discloses a method which comprises hydroformylating a functional group-containing mono or other olefine in water or a hydrous solvent using a water-soluble sulfonated phosphine and separating the product aldehyde by decantation or extraction. Further, Japanese Patent Application Laid-Open No. 157739/1983 and No. 216138/1983 each teaches a method which comprises hydroformylating 7-octen-1-al, 1,5-hexadiene or 1,7-octadiene in an aqueous solution of sulfolane or 1,4-butanediol in the presence of a water-soluble sulfonated phosphine and extracting the reaction mixture with a higher alcohol or a mixture thereof with a hydrocarbon. It is described therein that by the above method the infiltration of the catalyst and reaction solvent into the extract can be prevented and that only the straight-chain α,ω-dialdehyde can be selectively extracted and separated as the hemi-acetal of the higher alcohol. Further, Japanese Patent Application Laid-Open No. 21638/1983 teaches a method which comprises hydroformylating α,ω-diolefin, α,ω-alkenal or the like ih a water-insoluble organic solvent such as toluene and contacting the resulting reaction mixture with an aqueous solution of alkali metal hydrosulfite such as sodium hydrosulfite. By this procedure, the α,ω-dialdehyde produced by hydroformylation is selectively extracted into the aqueous layer as the alkali metal hydrosulfite adduct.

It is stated in Japanese Patent Application Laid-Open No. 167937/1982 (U.S. Pat. No. 4,248,802) referred to above that functional group-containing monoolefins and other olefins can be used as starting compounds but this literature does not contain specific reference to the use of α,ω-diolefins containing 6 to 10 carbon atoms or α,ω-alkenals containing 7 to 11 carbon atoms. The research conducted by the present inventors showed that when these α,ω-diolefins or α,ω-alkenals are used as reactants, the hydroformylation method described in Japanese Patent Application Laid-Open No. 167937/1982 (U.S. Pat. No. 4,248,802) does not give satisfactory results. Thus, since the starting material α,ω-diolefin or α,ω-alkenal is sparingly soluble in water, the hydroformylation reaction hardly proceeds when water is used as the reaction solvent, for the contact between the starting material and the rhodium catalyst dissolved in water is poor. When a mixture of water and a water-miscible organic solvent is used as the reaction solvent, the hydroformylation reaction rate can be improved by increasing the solubility of α,ω-diolefin or α,ω-alkenal in the reaction solvent. However, it has been found that when the hydroformylation of an α,ω-diolefin or α,ω-alkenal is conducted in a homogeneous reaction system using a mixture of water with an organic solvent (such as ethyl alcohol, acetone, acetonitrile, dimethoxyethane etc.) as specifically mentioned in Japanese Patent Application Laid-Open No. 167937/1982 (U.S. Pat. No. 4,248,802), the reaction proceeds anyway but when the reaction mixture is extracted with any of the solvents specifically mentioned (diethyl ether, benzene or toluene) in the same patent literature, the reaction solvent and catalyst find their way into the extract in large quantities to preclude a selective extraction of the desired product α,ω-dialdehyde. If a large amount of the catalyst component is extracted along with the desired product in such an extraction process, the subsequent distillative process for the purification of the product from the extract entails the inactivation of the extracted catalyst, so that such a production system is quite disadvantageous for commercial implementation. In order that the hydroformylation and subsequent extractive separation of the product from the catalyst may be advantageously accomplished on a commercial scale, it is necessary to find a suitable combination of a reaction solvent which is capable of assuring a sustained commercially satisfactory reaction rate for the hydroformylation of a specific olefin with an extractant which is capable of selective separation of the hydroformylation product.

The methods described in Japanese Patent Application Laid-Open No. 157739/1983 and No. 216138/1983 each comprises carrying out the hydroformylation of an α,ω-diolefin or α,ω-alkenal and the subsequent extraction and separation of the straight-chain α,ω-dialdehyde from the reaction mixture using a combination of a certain reaction solvent with a certain extractant and as such provides advantageous procedures for the production of straight-chain α,ω-dialdehydes. However, these methods of necessity call for subjecting the hemiacetal essentially composed of higher alcohol and the straight-chain α,ω-dialdehydes to distillation after extraction to decompose to α,ω-dialdehyde and, as a consequence, not only requires a step for recovery of the higher alcohol but entails partial conversion of the α,ω-diadehyde to the acetal compound in the course of distillation, thus tending to lower the yield of the α,ω-dialdehyde.

The method described in Japanese Patent Application Laid-Open No. 21638/1983 requires a time-consuming step for decomposition of the alkali metal hydrosulfite adduct in the separation of the desired α,ω-dialdehyde from the aqueous layer of the extract and entails a large consumption of alkali metal hydrosulfite, thus being economically disadvantageous.

SUMMARY OF THE INVENTION

It is an object of this invention to provide a commercially advantageous process for producing α,ω-dialdehydes from α,ω-diolefins or α,ω-alkenals.

It is another object of this invention to provide a process for producing α,ω-dialdehydes in high yield from readily available starting materials.

It is a further object of this invention is to provide a suitable combination of a reaction solvent which is capable of affording a commercially satisfactory reaction rate for the hydroformylation of a given olefin with an extractant which is capable of selective extraction of the hydroformylation product from the resulting reaction mixture, which combination assures commercially advantageous hydroformylation and subsequent separation of the catalyst from the reaction product.

In accordance with this invention, the abovementioned objects can be accomplished by a process for producing an α,ω-dialdehyde of the following formula (IV)

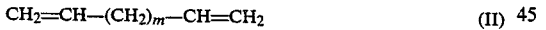

O=CH—E$^1$—(CH$_2$)$_m$—E$^2$—CH=O      (IV)

wherein E$^1$ and E$^2$ each independently represents a ethylene group or ethylidene group; m is a whole number of 2 to 6 which comprises:
(i) a hydroformylation step which comprises reacting an α,ω-diolefin of the following general formula (II)

CH$_2$=CH—(CH$_2$)$_m$—CH=CH$_2$      (II)

wherein m is as defined above or an α,ω-alkenal of the following general formula (III)

CH$_2$=CH—(CH$_2$)$_m$CH$_2$CH$_2$CHO      (III)

wherein m is as defined above with hydrogen and carbon monoxide for hydroformylation in aqueous sulfolane with a weight ratio of sulfolane to water in the range of 15/85 through 75/25 in the presence of a rhodium compound and, based on each gram atom of rhodium in said rhodium compound, 10 to 300 moles of a monodentate phosphine of the general formula (I)

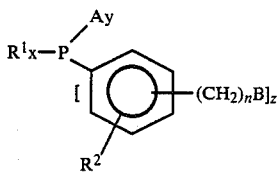

wherein R$^1$ is a saturated C$_{1-8}$ aliphatic hydrocarbon group, a saturated alicyclic hydrocarbon group or a substituted or unsubstituted aromatic hydrocarbon group; R$^2$ is a hydrogen atom, a methyl group, a methoxy group or a halogen atom; n is a whole number of 0 or 1, x is a whole number of 0, 1 or 2; y and z each is a whole number of 0, 1, 2 or 3 (provided that y and z are not concurrently equal to 0 and that $x+y+z=3$); A is

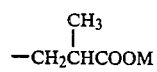

$$\begin{array}{c} CH_3 \\ | \\ -CH_2CHCOOM \end{array}$$

or —C(CH$_3$)$_2$COOM and B is —SO$_3$M or —COOM (where M is an alkali metal);
(ii) an extraction step which comprises extracting the reaction mixture obtained in the above step (i) with a saturated alicyclic hydrocarbon of 5 to 10 carbon atoms in a mixed gas atmosphere of hydrogen and carbon monoxide at a temperature not less than 40° C. to separate it into an extract layer(upper layer) containing the dialdehydes and an extraction residue(-lower layer); and
(iii) a recycling step which comprises recycling the extraction residue containing the catalyst component as obtained in the above step (ii) to the hydroformylation step (i).

DETAILED DESCRIPTION OF THE INVENTION

The α,ω-diolefin of general formula (II) which is employed as a starting material in the process of this invention is exemplified by 1,5-hexadiene, 1,7-octadiene, 1,9-decadiene, and so on. The α,ω-alkenal of general formula (III) is exemplified by 6-hepten-1-al, 7-octen-1-al, 8-nonen-1-al, 10-undecen-1-al, and so on. The rhodium compound to be used in the hydroformylation reaction according to this invention may be any rhodium compound wich acts as a hydroformylation catalyst under the conditions of the reaction. As examples of such rhodium compound, there may be mentioned rhodium carbonyl complex compounds of the general formula HRh(CO)(PR$_3^3$)$_3$ wherein R$^3$ is an aromatic hydrocarbon group, such as HRh(CO)[P(C$_6$H$_5$)$_3$]$_3$, and rhodium carbonyl clusters such as Rh$_4$(CO)$_{12}$, Rh$_6$(CO)$_{16}$ and so on. Other rhodium compounds such as RhCl[P(C$_6$H$_5$)$_3$]$_3$, rhodium acetylacetonate, rhodium acetate, rhodium chloride, rhodium oxide, etc. may also be used after activation by the conventional procedure in a separate catalyst preparation vessel. The rhodium compound is generally used in the concentration range of 0.05 to 10 milligram atoms as rhodium per liter of the hydroformylation reaction mixture.

Referring to the general formula (I) representing the monodentate phosphine to be employed in accordance with this invention, R$^1$ is a saturated C$_{1-8}$ hydrocarbon group, a saturated alicyclic hydrocarbon group or a substituted or unsubstituted aromatic hydrocarbon group. Specific examples of said saturated C$_{1-8}$ hydrocarbon group include methyl, ethyl, n-propyl, isopropyl, n-butyl, t-butyl, n-octyl, and so on. Specific examples of said saturated alicyclic hydrocarbon group include cyclohexyl, methylcyclohexyl and so on. Specific examples of said aromatic hydrocarbon group include phenyl, benzyl, tolyl and so on. The aromatic hydrocarbon group may be substituted by methoxy, chloro, cyano, nitro and so on. Referring, further, to general formula (I), M in —SO₃M or —COOM which is represented by B means an alkali metal, which may for example be lithium, sodium or potassium. Referring, further, to general formula (I), the phosphine in which B is —SO₃M or —COOM is generally used in the form of alkali metal salt but in lieu of using such an alkali metal salt, the corresponding carboxylic acid or sulfonic acid or an ester thereof may be used as converted to the alkali metal salt by reacting it with the hydroxide, bicarbonate, carbonate or the like of the alkali metal either in the reaction system or in a separate reaction vessel. Among monodentate phosphines of general formula (I), those which are particularly preferred are diaryl- or triarylphosphines wherein R¹ is an aromatic hydrocarbon, n is 0 or 1, x is 0, 1 or 2, y is 0 or 1, and z is 0, 1, 2 or 3 (provided that y and z are not concurrently 0 and x+y+z=3). The following is a partial listing of monodentate phosphines of general formula (I)

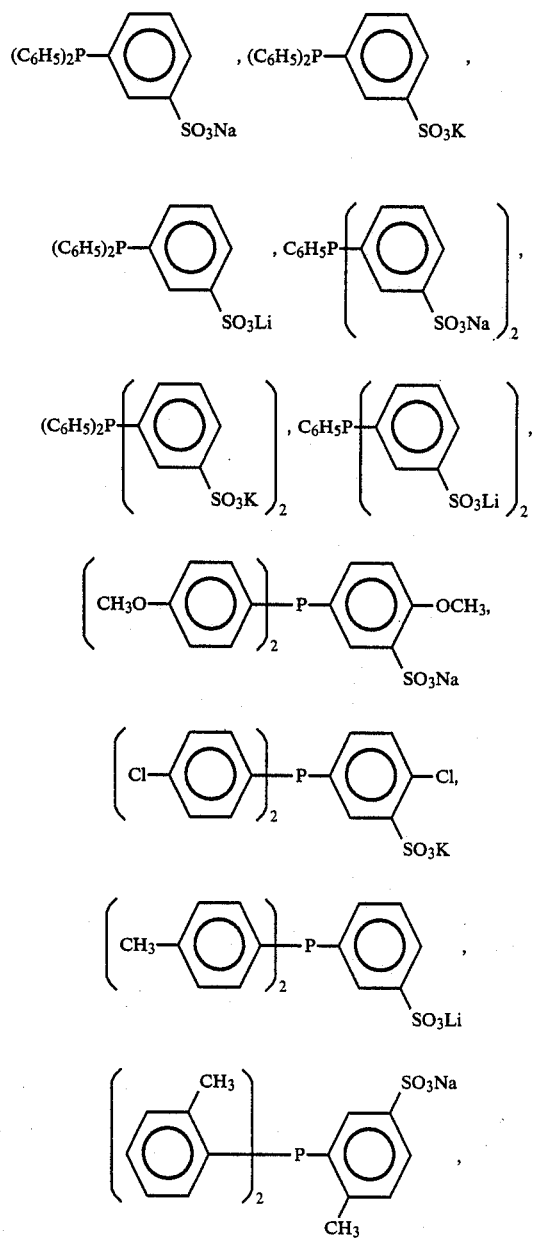

-continued (C₆H₅)₂PCH₂CH(CH₃)COONa, (C₆H₅)₂PCH₂CH(CH₃)COOK, (C₆H₅)₂PCH₂CH(CH₃)COOLi The monodentate phosphine is used in the range of 10 to 300 moles per gram atom of rhodium and preferably in the range of 30 to 250 moles on the same basis.

The hydroformylation reaction according to this invention is conducted in aqueous sulfolane with a weight ratio of sulfolane to water in the range of 15/85 through 75/25. The reaction rate is low when the concentration of sulfolane in the aqueous sulfolane is less than 15 weight percent. Conversely when the sulfolane concentration exceeds 75 weight percent, large proportions of the sulfolane and catalyst component are extracted out in the extraction procedure following the reaction. The particularly desirable weight ratio of sulfolane to water lies in the range of 25/75 through 60/40. The hydroformylation reaction according to this invention is carried out at a temperature generally in the range of 40° to 110° C. and preferably in the range of 60° to 90° C. The mole ratio of hydrogen to carbon monoxide in the mixed gas used for hydroformylation is generally in the range of ½ to 5/1 in terms of input gas composition.

Other gases inert to the hydroformylation reaction, such as methane, ethane, propane, nitrogen, helium, argon, carbon dioxide, etc., may be concomitantly present in the reaction system. The reaction pressure is generally selected from the range of 1 to 200 atmospheres but, for the purpose of assuring a high selectivity for straight-chain α,ω-dialdehydes, is preferably within the range of 1 to 30 atmospheres.

Since the solubility of the α,ω-diolefin or α,ω-alkenal in the reaction mixture under the conditions of this reaction is comparatively low, it is preferable to control the feeding rate of α,ω-diolefin or α,ω-alkenal so as to prevent heterogeneity of the reaction system in order that the operation may be conducted smoothly and the activity of the rhodium catalyst in the reaction system may be stabilized. As regards the concentration of the α,ω-dialdehyde in the reaction mixture, it is preferably within the range of 0.5 to 3 moles/liter from the standpoints of catalyst activity, separation of the product, and so forth.

The activity of the catalyst in the hydroformylation reaction system may be kept stable by conducting the reaction while the pH of the reaction mixture is maintained within the range of 5 to 7 by allowing a buffer such as, typically, a mixture of sodium dihydrogen phosphate and sodium hydrogen phosphate to be present in the hydroformylation reaction system.

The α,ω-dialdehyde of the general formula (IV) which is obtained in the process of this invention is exemplified by straight-chain alkanedial such as 1,8-octanedial, 1,9-nonanedial, 1,10-decanedial, 1,12- dodecanedial and the like; methylalkanedial such as 2-methyl-1,7-heptanedial, 2-methyl-1,8-octanedial, 2-methyl-1,9-nonanedial, 2-methyl-1,11-undecanedial; dimethylalkanedial such as 2,5-dimethyl-1,6-hexanedial, 2,7-dimethyl-1,8-octanedial, 2,9-dimethyl-1,10-decanedial.

The reaction mixture obtained by the above hydroformylation reaction is then subjected to an extraction procedure. The saturated $C_{5-10}$ alicyclic hydrocarbon to be employed as an extractant in this extraction step according to this invention is exemplified by cyclopentane, cyclohexane, methylcyclohexane, decalin and so on, although cyclohexane is particularly desirable in view of availability, boiling point and other factors. The amount of said extractant is, by volume, in the range of 1/5 to 3/1 and preferably in the range of ½ to 2/1, based on the volume of the hydroformylation reaction mixture. If the amount of the extractant is less than 1/5 of the volume of the reaction mixture, the extraction yield of the desired product is unacceptably low. Conversely if the amount of the extractant is in excess of 3/1 of the volume of the reaction mixture, a large volume of the extractant must be recovered at the separation of the product, thus entailing an economic disadvantage due to the high cost of recovery.

The extraction temperature according to this invention is not less than 40° C. While there is no critical upper limit of extraction temperature, the extraction is generally conducted at a temperature not exceeding the reaction temperature in consideration of the relation between the extraction temperature and the pressure of the hydrogen-carbon monoxide gas in the extraction system which is described hereinafter and the absence of any advantage of conducting the extraction at a temperature exceeding the reaction mixture. After all, the extraction is preferably conducted at a temperature in the range of 40° to 110° C. and more preferably at a temperature in the range of 50° to 100° C. If the extraction temperature is less than 40° C., the rate of extraction of the α,ω-dialdehyde into the extractant is too low for commercial purposes.

The extraction procedure is carried out in a mixed gas of hydrogen and carbon monoxide. The mole ratio of hydrogen to carbon monoxide in this mixed gas is in the range of 1/10 to 10/1 and preferably 1/5 to 5/1. If the mole ratio of hydrogen to carbon monoxide is less than 1/10 or exceeds 10/1, the catalyst is partially inactivated. The same is true when any of hydrogen gas, carbon monoxide gas, and inert gases such as nitrogen, carbon dioxide, argon, etc. is used alone. As the atmosphere for the extraction procedure, it is commercially advantageous to utilize the off gas from the reaction system. Within the range not adversely affecting the extraction procedure, there may be present inert gases such as nitrogen, helium, argon and the like in the extraction system. There is no critical upper limit to the pressure within the extraction system and this pressure is generally selected from the range of 1 to 30 atmospheres as the partial pressure of hydrogen and carbon monoxide. The pressure within the extraction system, in correlation with the extraction temperature, has an influence on the stability of the catalyst in the extraction system. Thus, while a comparatively high pressure is generally advantageous when the extraction temperature is high, a pressure within the range of 3 to 5 atmospheres is generally sufficient to maintain the catalyst activity stable when the extraction temperature is in the range of 50° to 100° C. It is commercially preferable to conduct the extraction in a continuous sequence but it may be conducted by the batch method.

In the extraction procedure according to this invention, the product α,ω-dialdehyde or the like and the unreacted starting compound olefin are extracted into the extract layer (upper layer), while the catalyst component is separated into the extraction residue (lower layer). The extraction residue layer is recycled, either as it is or after the known catalyst activation procedure, to the hydroformylation step.

The extract, either as it is or after washing with a small quantity of water, is subjected to distillation for removal of the extractant and the residue is subjected to vacuum distillation, whereby the α,ω-dialdehyde of high purity can be easily isolated. The extractant recovered in the process can be reused by recycling it to the extraction step. It is also possible to recover the the unreacted starting material and intermediate α,ω-diolefin and α,ω-alkenal by distillation and the α,ω-diolefin and α,ω-alkenal so recovered can be reused as starting materials by recycling them to the hydroformylation step. When the α,ω-dialdehyde is to be chemically derived into the corresponding alkanediol, alkanedicarboxylic acid, alkanediamine or the like, the above-mentioned extract, either as it is or after washing with a small quantity of water, can be subjected to reduction, oxidation or amination without distillative removal of the extractant.

The following examples are intended to illustrate this invention in further detail and should by no means be construed as limiting the invention in any manner.

EXAMPLE 1

A 1-liter stainless steel autoclave fitted with a thermometer, electromagnetic stirrer, a gas inlet and a gas outlet was charged with 0.125 mM of $Rh_4(CO)_{12}$, 50 mM of

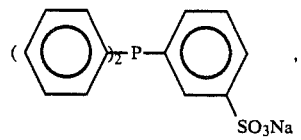

250 ml of water and 250 ml of sulfolane. After sufficient purging with hydrogen-carbon monoxide (mole ratio 2/1), the charge was heated to a constant internal temperature of 75° C. under stirring, with the internal pressure and exit gas flow rate being controlled at 10 atmospheres and 10 liters/hour, respectively, using the same mixed gas. The charge was further stirred at that temperature for 30 minutes. Then, with vigorous stirring, 64.3 g of 7-octen-1-al (500.1 mM, purity 98%, containing 2% of n-octanal) was continuously introduced into the autoclave via a constant-rate pump over one hour. After completion of this addition, the reaction mixture was further stirred for 1.5 hours. After a total of 2.5 hours of reaction, the stirring was discontinued and the autoclave was cooled. Thereafter, a small portion of the reaction mixture was withdrawn and analyzed by gas chromatography. As a result, the residual amount of 7-octen-1-al was 85.3 mM (82.6% conversion). It was also found that 348.5 mM of 1,9-nonanedial and 62.2 mM of 2-methyl-1,8-octanedial had been produced. This reaction mixture was then transported under pressure through a pipe without exposure to atmospheric air into a pressure-resistant glass autoclave controlled at an internal pressure of 3 atmospheres with hydrogen-carbon monoxide (mole ratio 1/1). With 250 ml of cyclohexane introduced into this glass autoclave, the internal temperature was adjusted to 65° C., with the internal pressure being kept at 3 atmospheres and the mixture was stirred for 5 minutes. On suspension of stirring, th reaction mixture immediately separated into two layers. The system was allowed to stand for 5 minutes and the upper cyclohexane layer was withdrawn through a pipe by utilizing the internal pressure. To the pressure-resistant autoclave containing the lower layer as maintained at an internal pressure of 3 atmospheres and an internal temperature of 65° C., there was added 250 ml of fresh cyclohexane and the mixture was stirred under the same conditions for 5 minutes and, then, allowed to stand for 5 minutes. The upper cyclohexane layer was withdrawn from the autoclave and mixed with the cyclohexane layer previously withdrawn and analyzed for substances extracted into it. Gas chromatographic analysis revealed that the extract contained 80.0 mM of the starting material 7-octen-1-al, 219 mM of product 1,9-nonanedial and 42.9 mM of product 2-methyl-1,8-octanedial. Based on these data, 63.7% of the product $\alpha,\omega$-dialdehyde(1,9-nonanedial and 2-methyl-1,8-octanedial) was extracted. The amount of sulfolane extracted into the extractant was 8.8 g. The analysis for rhodium and phosphorus compounds by atomic absorption spectrometry and colorimetry showed that the amounts of rhodium and phosphorus compounds extracted into the extractant were 0.05 ppm as atomic rhodium and 2.6 ppm as atomic phosphorus, respectively. Then, 7 ml of sulfolane was added to the catalyst layer remaining in the glass autoclave and the mixture was transfered to the above-mentioned stainless steel autoclave (reaction vessel) by utilizing the pressure differential with protection against exposure to the air. Then, under the same conditions as the first run, 64.3 g of 7-octen-1-al was continuously fed to the reactor over an hour and the reaction was further continued for 1.5 hours. Then, the same extraction procedure as in the first run was carried out. As a result, 7-octen-1-al, 1,9-nonanedial and 2-methyl-1,8-octanedial were extracted into the cyclohexane layer in the amounts of 84.4 mM, 288 mM and 54.8 mM, respectively. The amount of sulfolane extracted into the extractant was 9.8 g and the extracted amounts of rhodium and phosphorus compounds were 0.041 ppm as atomic rhodium and 2.0 ppm as atomic phosphorus. To the residual layer was added 7.8 ml of sulfolane, and the same reaction and extraction procedures as the above second run were repeated up to a total of 5 times. During this period, the rhodium catalyst and phosphine compound were not supplemented, although 7.8 ml of sulfolane was added to each residual layer. Table 1 shows the results of analysis for the compound extracted into the cyclohexane layers in the third, fourth and fifth runs.

TABLE 1

| Run | 7-Octen-1-al (mM) | 1,9-Nonanedial (mM) | 2-Methyl-1,8-octanedial (mM) | Sulfolane (g) | Rh (ppm) | P compound[1] (ppm) |
|---|---|---|---|---|---|---|
| 3rd | 84.0 | 329 | 60.7 | 10.2 | 0.040 | 2.1 |
| 4th | 86.6 | 340.7 | 61.7 | 10.0 | 0.035 | 1.8 |
| 5th | 86.0 | 345 | 62.1 | 10.3 | 0.037 | 1.8 |

Note
[1]Concentrations as atomic phosphorus

EXAMPLES 2–4 and AND COMPARATIVE EXAMPLES 1–8

The first run of reaction and extraction described in Example 1 was repeated except that the kind of extractant and the extraction temperature were varied as shown in Table 2. The results are set forth in Table 2.

TABLE 2

| Example or Comparative Example | Extractant | Extraction temperature (°C.) | % dialdehyde extracted[1] | Extracted into extractant | |
|---|---|---|---|---|---|
| | | | | Sulfolane (g) | Rh (ppm) |
| Example 2 | Methylcyclohexane | 50 | 59 | 7.6 | 0.031 |
| Example 3 | Cyclopentane | 75 | 66 | 9.3 | 0.050 |
| Example 4 | Decalin | 70 | 60 | 8.8 | 0.050 |
| Comparative Example 1 | Cyclohexane | 10 | 12 | 2.5 | 0.012 |
| Comparative Example 2 | Cyclohexane | 30 | 29 | 5.3 | 0.030 |
| Comparative Example 3 | Benzene | 50 | 87 | 165.0 | 0.711 |
| Comparative Example 4 | n-Hexane | 50 | 18 | 1.6 | 0.010 |
| Comparative Example 5 | n-Hexane | 25 | 10 | 1.3 | 0.011 |
| Comparative Example 6 | Diethyl ether[2] | 40 | 65 | 108.0 | 0.620 |
| Comparative Example 7 | Methyl isobutyl ketone[2] | 50 | 84 | 150.0 | 0.682 |
| Comparative Example 8 | n-Butyl acetate[2] | 50 | 47 | 43.0 | 0.155 |

Notes
[1]Dialdehyde: 1,9-nonanedial and 2-methyl-1,8-octanedial
[2]The residual layer after extraction contains a large amount of the extractant.

EXAMPLE 5

The same reactor as used in Example 1 was charged with 0.1 mM of $Rh_6(CO)_{16}$, 45 mM of

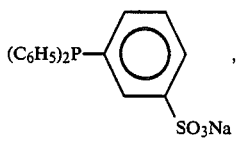

250 ml of water, and 250 ml of sulfolane, and after complete purging of the autoclave with hydrogen-carbon monoxide (mole ratio 3/1), the autoclave was heated until a constant internal temperature of 80° C. was established, with the internal pressure of the autoclave being maintained at 10 atmospheres using the above mixed gas. The stirring was further continued for 30 minutes, after which, with vigorous stirring, 40 g (364 mM) of 1,7-octadiene was continuously fed to the autoclave by means of a constant-rate pump over 1.5 hours. After completion of the addition, the stirring was further continued for 1.5 hours. During this reaction, hydrogen-carbon monoxide gas (mole ratio 3/1) was introduced into the autoclave via a pressure regulating valve so as to maintain the internal pressure of the autoclave at 10 atmospheres and the exit gas flow rate at 10 liters/hour. After a total of 3 hours of reaction, a small portion of the reaction mixture was sampled out and analyzed by gas chromatography. It was found that the residual amount of unreacted 1,7-octadiene was 57.5 mM (84.2% conversion) and that the output of 1,10-decanedial was 152 mM. In addition, 2-methyl-1,9-nonanedial, 2,7-dimethyl-1,8-octanedial, 8-nonen-1-al and 2-methyl-7-octen-1-al were detected in the amounts of 35 mM, 3 mM, 104 mM and 12 mM, respectively. Then, the extraction procedure was carried out in the same manner as Example 1 and the resulting cyclohexane layer was analyzed by gas chromatography. The extracted amounts of 1,7-octadiene, 1,10-decanedial, 2-methyl-1,9-nonanedial, 2,7-dimethyl-1,8-octanedial, 8-nonen-1-al, and 2-methyl-7-octen-1-al were 54.6 mM, 98.0 mM, 22.6 mM, 1.9 mM, 85.2 mM, and 9.9 mM, respectively. Based on these data, it was found that 64.7% of dialdehyde was extracted. Analysis for rhodium and phosphorus compounds by atomic absorption spectrometry and colorimetry showed that the amounts of rhodium and phosphorus compounds extracted into the extractant were 0.04 ppm as atomic rhodium and 2.3 ppm as atomic phosphorus. Then, 5 ml of sulfolane was added to the residual layer(raffinate layer) and the mixture was transferred to the reactor by utilizing the pressure differential, avoiding exposure to the air. Then, 40 g of 1,7-octadiene was continuously fed to the reactor under the same conditions as in the first run and the extraction was also carried out in the same manner as the first run. In this manner, the reaction and subsequent extraction were carried out for a total of 5 times. During this period, the catalyst and phosphine were not supplemented, although 7.5 ml of sulfolane was added to each residual layer. Table 3 shows the results of analysis for the compounds extracted into the cyclohexane layers in the second and subsequent runs.

TABLE 3

| Run | 1,7-Octadiene (mM) | 1,10-Decanedial (mM) | 2-Methyl-1,9-nonanedial (mM) | 2,7-Dimethyl-1,8-octanedial (mM) | 8-Nonene-1-al (mM) | 2-Methyl-7-octen-1-al (mM) | Sulfolane (g) | Rh (ppm) | P compound (ppm)[1] |
|---|---|---|---|---|---|---|---|---|---|
| 2nd | 57.3 | 134 | 30.5 | 2.6 | 100.7 | 11.6 | 6.1 | 0.040 | 2.3 |
| 3rd | 57.5 | 147 | 33.7 | 2.9 | 104.6 | 12.0 | 7.4 | 0.035 | 1.8 |
| 4th | 57.5 | 149 | 34.6 | 2.9 | 105.0 | 12.1 | 7.3 | 0.035 | 1.8 |
| 5th | 57.2 | 148 | 34.5 | 2.8 | 104.7 | 11.8 | 7.3 | 0.035 | 1.8 |

Note
[1]Concentrations as atomic phosphorus

EXAMPLES 6-8 AND COMPARATIVE EXAMPLES 9-11

The reaction and extraction procedures of the first run according to Example 5 were repeated except that the extraction temperature and atmosphere were varied as shown in Table 4 and the extraction time was set at 2 hours. The resulting residual layer was further used in the second run of reaction in the same manner as Example 5. Table 4 shows the specific activity of the catalyst, i.e. the ratio of the conversion of 1,7-octadiene in the second reaction to that in the first reaction.

TABLE 4

| Example or Comparative Example | Conditions of extraction | | | Specific activity[1] |
|---|---|---|---|---|
| | Temperature (°C.) | Atmosphere | Pressure (atms.) | |
| Example 6 | 100 | CO/H$_2$(CO/H$_2$ = 2/1) | 10 | 0.99 |
| Example 7 | 80 | CO/H$_2$(CO/H$_2$ = 1/3) | 6 | 0.99 |
| Example 8 | 120 | CO/H$_2$(CO/H$_2$ = 1/1) | 15 | 0.99 |
| Comparative Example 9 | 70 | Nitrogen gas | 10 | 0.83 |
| Comparative Example 10 | 60 | Hydrogen gas | 5 | 0.79 |
| Comparative Example 11 | 60 | Carbon monoxide gas | 5 | 0.61 |

Note
[1]Specific activity = (the conversion of 1,7-octadiene in second reaction)/(the conversion of 1,7-octadiene in first reaction)

EXAMPLE 9

The same reactor as used in Example 1 was charged with 0.8 mM of HRh(CO)[P(C$_6$H$_5$)$_3$]$_3$, 50 mM of

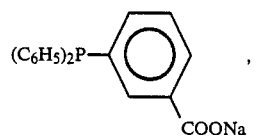

300 ml of water, and 200 ml of sulfolane and the hydroformylation of 7-octen-1-al was carried out in the same manner as Example 1 except that the pressure was maintained at 15 atmospheres with hydrogen-carbon monoxide (mole ratio 1/1) and the reaction temperature was maintained at 80° C. After completion of the reaction, the reaction mixture was analyzed by gas chromatography. It was found that the residual amount of unreacted 7-octen-1-al was 51.5 mM (90% conversion) and the outputs of 1.9-nonanedial and 2-methyl-1,8-octanedial were 376 mM and 71.0 mM, respectively. This reaction mixture was extracted under the same conditions as Example 1. As a result, 7-octen-1-al, 1,9-nonanedial and 2-methyl-1,8-octanedial were extracted into the extractant in the amounts of 49.9 mM, 236 mM and 51.8 mM, respectively (64.4% extracted). The amount of sulfolane extracted into the extractant was 8.2 g and the extracted amounts of rhodium and phosphorus compounds were 0.06 ppm as atomic rhodium and 3.5 ppm as atomic phosphorus.

EXAMPLE 10

The same reactor as used in Example 5 was charged with 0.25 mM of $Rh_4(CO)_{12}$, 100 mM of

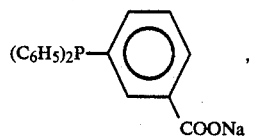

300 ml of water and 200 ml of sulfolane, and heated. Then, 41 g (500 mM) of 1,5-hexadiene was continuously fed to the autoclave over an hour. After completion of the addition, the reaction was further continued for 2.5 hours but otherwise under the same conditions as Example 5. After completion of the reaction, the reaction mixture was analyzed by gas chromatography. As a result, it was found that the residual amount of 1,5-hexadiene was 15 mM (97% conversion) and that the outputs of 1,8-octanedial, 2-methyl-1,7-heptanedial, 2,5-dimethyl-1,6-hexanedial and 6-hepten-1-al were 310.4 mM, 69.8 mM, 7.8 mM and 87.3 mM, respectively. Then, the extraction procedure was carried out in the same manner as Example 5 except that the extraction temperature was set at 70° C. and the pressure maintained at 5 atmospheres using hydrogen-carbon monoxide (mole ratio 3/1). The extract contained 1,5-hexadiene, 1,8-octanediol, 2-methyl-1,7-heptanedial, 2,5-dimethyl-1,6-hexanedial and 6-hepten-1-al in the amounts of 13.5 mM, 192.4 mM, 43.3 mM, 4.9 mM and 69.8 mM, respectively (62% overall dialdehyde extracted). The amount of sulfolane extracted was 7.4 g and the extracted amounts of rhodium and phosphorus compounds were 0.05 ppm as atomic rhodium and 2.6 ppm as atomic phosphorus.

EXAMPLE 11

The reaction of Example 10 was repeated except that 69 g (500 mM) of 1,9-decadiene was used as the starting material diene. After completion of the reaction, the reaction mixture was analyzed by gas chromatography. As a result, the residual amount of 1,9-decadiene was 30 mM (94% conversion) and the outputs of 1,12-dodecanedial, 2-methyl-1,11-undecanedial, 2,9-dimethyl-1,10-decanedial and 10-undecen-1-al were 277.9 mM, 61.7 mM, 3.5 mM and 114.3 mM, respectively. Then, the extraction was carried out under the same conditions as Example 10. The extract contained 1,9-decadiene, 1,12-dodecanedial, 2-methyl-1,11-undecanedial, 2,9-dimethyl-1,10-decanedial and 10- undecen-1-al in the amounts of 28.5 mM, 180.6 mM, 40.1 mM, 2.3 mM and 99.4 mM, respectively (65% overall dialdehyde extracted). The amount of sulfolane extracted into the extractant was 8.0 g and the extracted amounts of rhodium and phosphorus compounds were 0.04 ppm as atomic rhodium 3.3 ppm as atomic phosphorus.

COMPARATIVE EXAMPLE 12

The reaction procedure of Exmple 4 was repeated except that 500 ml of water was used in lieu of water-sulfolane as the reaction solvent. After completion of the reaction, the reaction mixture was analyzed by gas chromatography. It was found that the residual amount of unreacted 1,7-octadiene was 480 mM (4% conversion), indicating that substantially no reaction had taken place.

What is claimed is:

1. A process for producing an α,ω-dialdehyde of the following general formula (IV)

$$O=CH-E^1-(CH_2)_m-E^2-CH=O \qquad (IV)$$

wherein $E^1$ and $E^2$ each independently represents a ethylene group or ethylidene group; m is a whole number of 2 to 6 which comprises:

(i) a hydroformylation step which comprises reacting an α,ω-diolefin of the following general formula (II)

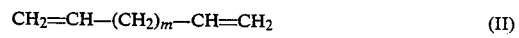

$$CH_2=CH-(CH_2)_m-CH=CH_2 \qquad (II)$$

wherein m is as defined above or an α,ω-alkenal of the following general formula (III)

$$CH_2=CH-(CH_2)_mCH_2CH_2CHO \qquad (III)$$

wherein m is as defined above with a gaseous mixture of hydrogen and carbon monoxide in a mixture of water and sulfolane with a weight ratio of sulfolane to water in the range of 15/85 through 75/25 in the presence of a rhodium compound and, based on each gram-atom of rhodium in said rhodium compound, 10 to 300 moles of a monodentate phosphine of the general formula (I)

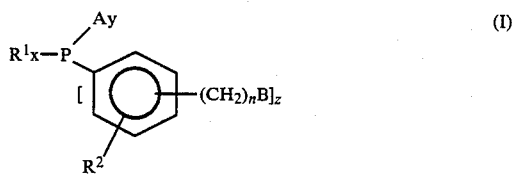

wherein $R^1$ is a saturated $C_{1-8}$ aliphatic hydrocarbon group, a saturated alicyclic hydrocarbon group or a substituted or unsubstituted aromatic hydrocarbon group; $R^2$ is a hydrogen atom, a methyl group, a methoxy group or a halogen atom; n is a whole number of 0 or 1, x is a whole number of 0, 1 or 2; y and z each is a whole number of 0, 1, 2 or 3 (provided that y and z are not concurrently equal to 0 and that $x+y+z=3$; A is

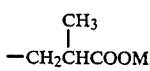

or $-C(CH_3)_2COOM$ and B is $-SO_3M$ or COOM, (where M is an alkali metal;

(ii) an extraction step which comprises extracting the reaction mixture obtained in the above step (i) with a saturated alicyclic hydrocarbon of 5 to 10 carbon atoms in a mixed gas atmosphere of hydrogen and carbon monoxide at a temperature not less than 40° C. to separate it into an extract layer containing the dialdehydes and an extraction residue; and (iii) a recycling step which comprises recycling the extraction residue containing the catalyst as obtained in the above step (ii) to the hydroformylation step (i).

2. The process of claim 1 wherein said rhodium compound is used in the range of 0.05 to 10 milligram atoms of rhodium per liter of the reaction mixture in said hydroformylation step.

3. The process of claim 1 wherein said monodentate phosphine is a diarylphosphine or triarylphosphine.

4. The process of claim 1 wherein said monodentate phosphine is used in the range of 30 to 250 moles per gram atom of rhodium.

5. The process of claim 1 wherein said aqueous sulfolane has a weight ratio of sulfolane to water in the range of 25/75 through 60/40.

6. The process of claim 1 wherein said hydroformylation reaction is carried out at a temperature in the range of 40° to 110° C.

7. The process of claim 1 wherein said hydroformylation reaction is carried out at a temperature in the range of 60° to 90° C.

8. The process of claim 1 wherein said gaseous mixture of hydrogen and carbon monoxide has a mole ratio of hydrogen to carbon monoxide in the range of 1/2 to 5/1.

9. The process of claim 1 wherein the concentration of $\alpha,\omega$-dialdehyde in said reaction mixture is in the range of 0.5 to 3 moles/liter.

10. The process of claim 1 wherein the saturated alicyclic hydrocarbon used in step (ii) is cyclohexane.

11. The process of claim 1 wherein the extraction in step (ii) is performed at a temperature in the range of 50° to 100° C.

12. The process of claim 1 wherein the extraction in step (ii) is performed at a temperature in the range of 40° to 110° C.

13. The process of claim 1 wherein the extraction in step (ii) is performed in an atmosphere of hydrogen and carbon monoxide with a mole ratio of hydrogen to carbon monoxide in the range of 1/10 to 10/1.

14. The process of claim 1 wherein the extraction in step (ii) is performed with an atmosphere of hydrogen and carbon monoxide with a mole ratio of hydrogen to carbon monoxide in the range of 1/5 to 5/1.

15. The process of claim 1 wherein the extraction in step (ii) is performed in the range of 3 to 5 atmospheres.

* * * * *

UNITED STATES PATENT AND TRADEMARK OFFICE
CERTIFICATE OF CORRECTION

PATENT NO. : 4,808,756

DATED : Feb. 28, 1989

INVENTOR(S) : Yasuo TOKITOH, et al.

It is certified that error appears in the above-identified patent and that said Letters Patent is hereby corrected as shown below:

On the title page
The entry for [30] Foreign Application Priority Data should be deleted. Priority was not claimed in the application.

Signed and Sealed this

Tenth Day of October, 1989

Attest:

DONALD J. QUIGG

Attesting Officer

Commissioner of Patents and Trademarks